United States Patent
Mitra (10) Patent No.: US 7,214,195 B2
(45) Date of Patent: May 8, 2007

(54) METHOD OF AND APPARATUS FOR DETECTING DISEASED TISSUE BY SENSING TWO BANDS OF INFRARED RADIATION

(75) Inventor: Pradip Mitra, Colleyville, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 467 days.

(21) Appl. No.: 10/625,155

(22) Filed: Jul. 23, 2003

(65) Prior Publication Data

US 2005/0020924 A1 Jan. 27, 2005

(51) Int. Cl.
*A61B 5/00* (2006.01)
(52) U.S. Cl. .................. 600/549; 600/473; 600/474
(58) Field of Classification Search ........ 600/473–475, 600/549
See application file for complete search history.

(56) References Cited

U.S. PATENT DOCUMENTS

| | | | | |
|---|---|---|---|---|
| 4,366,381 A | 12/1982 | Fischer et al. | ........... | 250/316.1 |
| 4,428,382 A | 1/1984 | Walsall et al. | ............. | 128/736 |
| 4,809,701 A | 3/1989 | Le Bihan et al. | ........... | 128/653 |
| 5,205,293 A | 4/1993 | Ito et al. | ..................... | 128/691 |
| 5,207,227 A | 5/1993 | Powers | ....................... | 128/691 |
| 5,233,994 A | 8/1993 | Shmulewitz | ........... | 128/661.08 |
| 5,445,157 A | 8/1995 | Adachi et al. | ............. | 128/664 |
| 5,539,206 A | 7/1996 | Schimert | ................. | 250/338.4 |
| 5,588,437 A | 12/1996 | Byrne et al. | ................ | 128/691 |
| 5,678,555 A | 10/1997 | O'Connell | ................ | 128/664 |
| 5,771,261 A | 6/1998 | Anbar | ........................ | 347/45 |
| 5,810,010 A | 9/1998 | Anbar | ........................ | 128/664 |
| 5,845,639 A | 12/1998 | Hochman et al. | ........ | 128/653.1 |

(Continued)

FOREIGN PATENT DOCUMENTS

EP 0 685 720 A1 12/1995

(Continued)

OTHER PUBLICATIONS

Michael Anbar, James C. Montoro, Kyu Ha Lee, and Sean D' Arcy, Manifestation of Neurological Abnormalities Through Frequency Analysis of Skin Temperature Regulation, *Thermology*, vol. 3, No. 1, pp. 234-241 (1988).

(Continued)

*Primary Examiner*—H. Q. Nguyen
(74) *Attorney, Agent, or Firm*—Daren C. Davis; James E. Walton (57) ABSTRACT

A method of and apparatus for detecting diseased tissue based upon infrared imaging in two different bands of infrared wavelengths is described. The use of two series of infrared images taken in two different bands of infrared wavelengths increases sensitivity to the subtle temperature changes caused by diseased skin and tissue, especially in the case of cancerous tissue. By sensing skin temperature, the homogeneity thereof, the time variations thereof and the correlation between the two series of infrared images, the present invention decreases the rate of false positives and false negatives. The increased discrimination due to two series of infrared images allows for reliable detection of diseased or cancerous tissue even in the presence of skin tone variations such as birthmarks, tattoos and freckles. The present invention finds special application in the field of breast cancer detection where subtle skin temperature variations may readily be sensed using two series of infrared images.

8 Claims, 4 Drawing Sheets

U.S. PATENT DOCUMENTS

| | | |
|---|---|---|
| 5,961,466 A | 10/1999 | Anbar .................. 600/474 |
| 5,999,843 A | 12/1999 | Anbar .................. 600/474 |
| 6,133,571 A | 10/2000 | Dodd ................. 250/338.4 |
| 6,157,042 A | 12/2000 | Dodd .................... 257/21 |
| 6,355,939 B1 | 3/2002 | Dodd .................... 257/21 |
| 2002/0146056 A1 | 10/2002 | Yano et al. |

FOREIGN PATENT DOCUMENTS

| | | |
|---|---|---|
| EP | 1 212 977 A1 | 6/2002 |
| WO | WO 02/47542 A2 | 6/2002 |

OTHER PUBLICATIONS

Shahram Hejazi, Omid A. Moghadam, Robert A. Spangler and Michael Anbar, Simultaneous Acquisition of Thermal and Visible Images in a Scanning Infrared Camera, *SPIE*, vol. 2020, pp. 510-516 (1993).

Michael Anbar and Robert F. Haverly, Local "Micro" Variance In Temperature Distribution Evaluated By Digital Thermography, *Biomedical Termology*, vol. 13, pp. 173-187 (1994).

Michael Anbar, a monograph entitled, Quantitative Dynamic Telethermometry in Medical Diagnosis and Management, CRC Press Inc., 4 pages, (Sep. 1994).

Michael Anbar, Hyperthermia of the cancerous breast: analysis of mechanism, *Cancer Letters*, vol. 84, No. 1, pp. 23-29 (Aug. 29, 1994).

Michael Anbar and Barton M. Gratt, Role of Nitric Oxide in the Phsiopathology of Pain, *Journal of Pain and Symptom Management*, vol. 14, No 4, pp. 225-242 (Oct. 4, 1997).

M. Anbar, M. W. Grenn, M. T. Marino, L. Milescu, and K. Zamani, Fast Dynamic Area Telethermometry (DAT) of the Human Forearm With a Ga/As Quantum Well Infrared Focal Plane Array Camera, *European Journal of Thermology*, pp. 105-118 (1997).

FIG. 10

METHOD OF AND APPARATUS FOR DETECTING DISEASED TISSUE BY SENSING TWO BANDS OF INFRARED RADIATION

FIELD OF THE INVENTION

The present invention relates to a method of and apparatus for detecting diseased tissue. In paticular, the present invention provides a noninvasive method of detecting diseased tissue by sensing skin temperature, the homogeneity thereof, the temporal variation thereof and the correlation thereof using a sensor detecting two different bands of infrared wavelengths.

BACKGROUND OF THE INVENTION

In the field of diseased or cancerous tissue detection, many methods require subjecting the patient to doses of X-ray radiation or to painful biopsies, especially for breast cancer detection. More recently, researchers discovered that dysfunction of the neuronal control of the vasculature due to cancerous lesions leads to temporal or periodic perfusion changes. By measuring, recording and analyzing these periodic perfusion changes, typically through infrared (IR) imaging, diseased or cancerous tissue can be detected. While these periodic perfusion changes appear to be associated with most types of diseased or cancerous tissue, skin cancer and other cancers near the surface of the skin are most likely to be detected using IR imaging. Such a method is described in U.S. Pat. Nos. 5,810,010, 5,961,466 and 5,999,843, all to Michael Anbar, and hereby incorporated by reference.

In particular, breast cancer appears to be very susceptible to detection through IR imaging. Breast cancer detection by this method involves taking a series of IR images of the breast. This series of IR images will show both neuronal control and non-neuronal control of periodic perfusion changes in a cancerous breast. These IR images are then converted into thermal images with a temperature associated with each portion of the thermal image. The thermal images are then analyzed by finding the average temperature and standard deviation of temperature for each subarea within the thermal images. Clusters of subareas having abnormal average temperatures or standard deviations are indicative of cancer. It is anticipated that breast cancer may generally be detected by imaging the appropriate lymph nodes, the so-called "signal nodes," which tend to have increased biological activity if cancer is present.

The frequency of the periodic perfusion changes can also be used to detect cancer. Neuronal control generally has a lower frequency than non-neuronal control of periodic perfusion. Therefore, by analyzing the thermal images and determining the periodic perfusion frequency for each of the subareas, clusters of subareas having higher frequencies are indicative of cancer.

The use of IR images for cancer detection places very stringent requirements on an IR imager. The small temperature changes associated with neuronal and non-neuronal perfusion require an IR imager sensitivity of less than 0.01° C. While IR imagers having this level of sensitivity have been demonstrated, these IR imagers have not successfully been built in quantity.

In view of the desirability of non-invasive means of cancer detection that do not require subjecting the patient to X-ray radiation exposure, there exists a need for a method that places lower requirements upon IR imager sensitivity. A method that requires lower sensitivity will lead to increased manufacturability and lower IR imager cost. Lower cost IR imagers can lead to greater accessibility to cancer screening and detection.

SUMMARY OF THE INVENTION

A first embodiment of the present invention comprises a method of detecting diseased tissue including recording first and second series of IR images of a predetermined area of tissue. The first and second series of IR images are recorded in corresponding first and second bands of IR wavelengths, the two bands of IR wavelengths being different. The first and second series of IR images are converted into corresponding first and second series of thermal images. The predetermined area of tissue is subdivided into a plurality of subareas. A first plurality of average temperature values is determined for each of the plurality of subareas from a corresponding one of the first series of thermal images. A first average temperature is determined using the first plurality of average temperature values. A second plurality of average temperature values is determined for each of the plurality of subareas from a corresponding one of the second series of thermal images. A second average temperature is determined using the second plurality of average temperature values. The resulting first and second pluralities of average temperature values for each of the plurality of subareas is then analyzed for possible diseased tissue. Tissue corresponding to a cluster of at least six adjacent subareas having a spatial distribution of corresponding first plurality of average temperature values that is less than about 20% or more than about 100% of the first average temperature is preliminarily determined to be diseased. Tissue corresponding to the cluster preliminarily determined to be diseased is further analyzed. If the cluster has a spatial distribution of corresponding second plurality of average temperature values that is less than about 20% or more than about 100% of the second average temperature, tissue corresponding to the cluster is confirmed to be diseased.

Another embodiment of the present invention comprises a method of detecting diseased tissue including recording first and second series of IR images of a predetermined area of tissue. The first and second series of IR images are recorded in corresponding first and second bands of IR wavelengths, the two bands of IR wavelengths being different. The first and second series of IR images are converted into corresponding first and second series of thermal images. The predetermined area of tissue is subdivided into a plurality of subareas. A first plurality of average temperature values and a first plurality of temperature standard deviations are determined for each of the plurality of subareas from a corresponding one of the first series of thermal images. A second plurality of average temperature values and a second plurality of temperature standard deviations are determined for each of the plurality of subareas from a corresponding one of the second series of thermal images. For each of the plurality of subareas, each corresponding one of the first plurality of average temperature values is divided by a corresponding one of the first plurality of temperature standard deviations to determine a corresponding one of a first plurality of homogeneity of skin temperature (HST) values for the plurality of subareas. For each of the plurality of subareas, each corresponding one of the second plurality of average temperature values is divided by a corresponding one of the second plurality of temperature standard deviations to determine a corresponding one of a second plurality of HST values for the plurality of subareas. A first average HST value is determined using the first plurality of HST values while a second average HST value is determined using the second plurality of HST values. The resulting first and second pluralities of HST values for each of the plurality of subareas are then analyzed for possible diseased tissue. Tissue corresponding to a cluster of at least six adjacent subareas having a corresponding spatial distribution of first plurality of HST values that is less than about 20% or more than about 100% of the first average HST value is preliminarily determined to be diseased. Tissue corresponding to the cluster preliminarily determined to be diseased is further analyzed. If the cluster has a corresponding spatial distribution of second plurality of HST values that is less than about 20% or more than about 100% of the second average HST value, tissue corresponding to the cluster is confirmed to be diseased.

In yet another embodiment, the present invention comprises a method of detecting diseased tissue including recording first and second series of infrared images of a predetermined area of tissue. The first and second series of infrared images are recorded in respective first and second bands of infrared wavelengths, with the second band of infrared wavelengths different from the first band of infrared wavelengths. The first and second series of infrared images are converted into corresponding first and second series of thermal images. The predetermined area of tissue is subdivided into a plurality of subareas. A first plurality of average temperature values is determined for each of the plurality of subareas, with each of the first plurality of average temperature values for each of the plurality of subareas being determined from one of the first series of thermal images. A second plurality of average temperature values is determined for each of the plurality of subareas, with each of the second plurality of average temperature values for each of the plurality of subareas being determined from one of the second series of thermal images. First and second radiance measurements are taken at respective first and second bands of infrared wavelengths of known healthy tissue. The first and second radiance measurements of known healthy tissue are correlated. The first and second plurality of average temperature values for each of the plurality of subareas are correlated. The correlated first and second plurality of average temperature values for each of the plurality of subareas is then analyzed. When a spatial distribution of slopes of the correlated first and second plurality of average temperature values corresponding to a cluster comprising at least six adjacent subareas is different from a slope of the correlation of known healthy tissue, tissue corresponding to the cluster is determined to be diseased.

In still another embodiment, the present invention comprises a method of detecting diseased tissue including recording first and second series of IR images of a predetermined area of tissue. The first and second series of IR images are recorded in corresponding first and second bands of IR wavelengths, the two bands of IR wavelengths being different. The first and second series of IR images are converted into corresponding first and second series of thermal images. The predetermined area of tissue is subdivided into a plurality of subareas. A first plurality of average temperature values and a first plurality of temperature standard deviations are determined for each of the plurality of subareas from a corresponding one of the first series of thermal images. A second plurality of average temperature values and a second plurality of temperature standard deviations are determined for each of the plurality of subareas from a corresponding one of the second series of thermal images. A first average temperature standard deviation is determined using the first plurality of temperature standard deviations. A second average temperature standard deviation is determined using the second plurality of temperature standard deviations. The resulting first and second pluralities of temperature standard deviations for each of the plurality of subareas are then analyzed for possible diseased tissue. Tissue corresponding to a cluster of at least six adjacent subareas having a spatial distribution of corresponding temperature standard deviations that is less than about 20% or more than about 100% of the first average temperature standard deviation is preliminarily determined to be diseased. Tissue corresponding to the cluster preliminarily determined to be diseased is further analyzed. If the cluster has a corresponding spatial distribution of second plurality of temperature standard deviations that is less than about 20% or more than about 100% of the second average temperature standard deviation, tissue corresponding to the cluster is confirmed to be diseased.

In further embodiments, alternative data analysis is possible. This alternative data analysis may include finding contributing frequencies for each subarea and determining that tissue corresponding to a cluster having a spatial distribution of less than a lower threshold frequency or more than an upper threshold frequency is diseased. The data may undergo fast Fourier analysis for this frequency determination. The data in the two series of thermal images can be correlated with diseased tissue having a different correlation intercept than healthy tissue. The contrast in the two series of IR images can be enhanced by subjecting the predetermined area of tissue to thermal stress, such as by directing a cooling flow of air across the area of tissue.

BRIEF DESCRIPTION OF THE DRAWINGS

The present invention is described in reference to the following Detailed Description and the drawings in which.

DETAILED DESCRIPTION OF THE PREFERRED EMBODIMENTS

Various embodiments of the present invention are described in detail with reference to the drawings. While the following description will generally discuss each embodiment separately, two or more embodiments may be combined to increase the accuracy of diseased or cancerous tissue detection. Further, while the present description will generally use only two bands of IR wavelengths, the use of three or more bands of IR wavelengths will further increase system sensitivity to diseased tissue.

Figure 1:
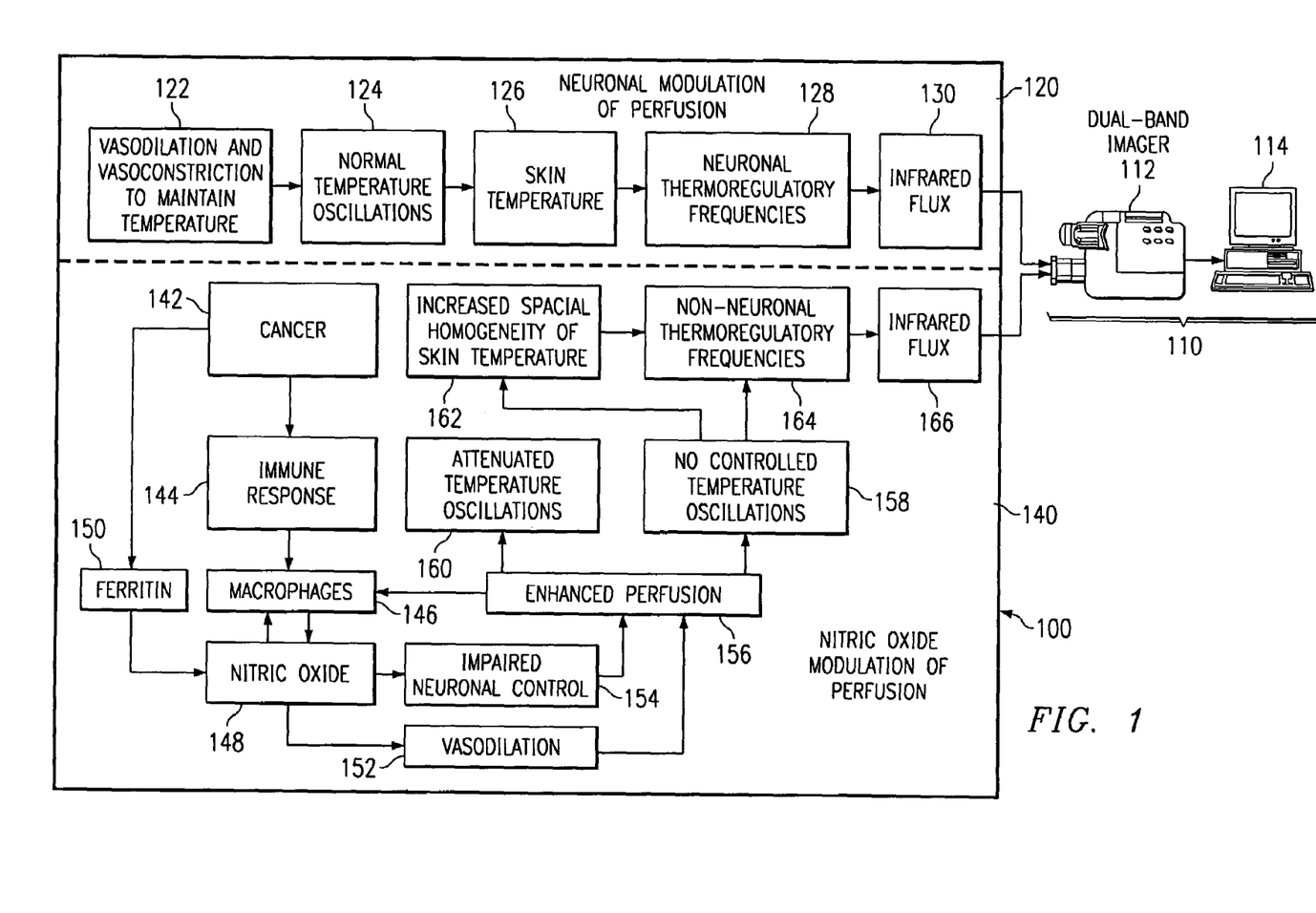
FIG. 1 is diagram of the blood perfusion process that can be detected by embodiments of the present invention.

FIG. 1 illustrates an area of tissue and skin 100, of which a portion is diseased, such as by a cancerous lesion. This area of tissue and skin 100 is imaged by a diagnostic system 110 employing the methodology of the present invention. The diagnostic system 110 comprises a dual-band IR imager 112 and a computer 114.

In the healthy portion of the area of tissue and skin 100, the body regulates its temperature using neuronal modulation of blood perfusion 120. The neuronal modulation of blood perfusion 120 includes vasodilation to cool the body and vasoconstriction to warm the body in the body's effort to maintain a desired temperature 122. This results in normal temperature oscillations 124 about the desired temperature 122. The body uses the skin as a radiator to remove excess heat causing the skin temperature 126 to oscillate. The skin temperature 126 oscillates over a band of neuronal thermoregulatory frequencies (TRFs) 128. The skin therefore radiates an IR flux 130 as excess heat is given off by the skin in the body's effort to maintain the desired temperature 122. While this process is generally discussed in terms that the tissue underlying the skin is cancerous, this method lends itself to the detection of skin cancer as well. For that reason, while the term tissue and skin may be used separately, skin will also be considered tissue for the purposes of this description.

The diagnostic system 110 takes a series of infrared images of the tissue and skin 100 using the dual-band IR imager 112 and processes the resultant images using the computer 114. The actual images will be composed of many individual pixels, each corresponding to a different portion of the imaged tissue and skin 100. The dual-band IR imager 112 may be based upon a 256 pixel by 256 pixel or 480 pixel by 640 pixel dual-band IR photodetector array. To increase sensitivity, the dual-band IR imager 112 images the tissue and skin 100 in two different bands of IR wavelengths resulting in two different series of IR images. By using the two different series of IR images, the occurrence of false positives and false negatives may be reduced. The second series of IR images in the second band of IR wavelengths may serve as a check on the first series of IR images in the first band of IR wavelengths, thereby increasing overall diagnostic system 110 sensitivity depending upon the data analysis method. The use of N independent bands of IR wavelengths generally leads to a $\sqrt{N}$ increase in sensitivity. With the two bands used throughout this description, this increase in sensitivity leads from a single band IR diagnostic system having a sensitivity of 30 m° C. to a dual-band IR diagnostic system 110 having a sensitivity of 21 m° C. Alternatively, if 30 m° C. is the desired diagnostic system 110 sensitivity, then the dual-band IR imager 112 can incorporate two single-band IR photodetector arrays each having a sensitivity of 42 m° C., thereby improving manufacturability.

The increased sensitivity of the dual-band IR imager 112 over a single-band IR imager decreases the occurrence of false positive and false negatives due to tissue and skin variations. Different portions of the skin may radiate different levels of IR flux, even though both the skin and the underlying tissue are healthy. As an example, a birthmark will likely radiate heat differently than normal skin. Similarly, a tattoo may create a false positive or false negative, as it too will radiate heat differently than normal skin. For a very sensitive single-band IR imager, a large freckle may lead to a false positive or false negative. However, by using two series of IR images, each taken in different bands of IR wavelengths, false positives and false negatives due to variations in skin color will be minimized. Variations in the underlying tissue can also affect detection of diseased tissue. While a breast may have relatively uniform tissue, an arm will include areas of significant muscle tissue adjacent to bony regions such as the elbow and wrist, resulting in IR image variations.

The nitric oxide (NO) modulation of blood perfusion 140 will be described next. A diseased portion of the tissue and skin 100, due to a cancer 142 in this discussion, provokes an immune response 144 within the tissue and skin 100. This immune response 144 results in increased macrophage activity 146, which produces NO 148. Some cancers, such as breast cancer, are known to elevate the local level of ferritin 150 within the diseased tissue. Elevated levels of ferritin 150 further increases the amount of NO 148 produced within the diseased tissue. Nitric oxide causes vasodilation 152 of the capillary bed leading to enhanced blood perfusion 156 within the diseased tissue. A side effect of the presence of NO is that neuronal control (vasodilation and vasoconstriction) of the capillary bed is impaired 154. The net result is that temperature in the diseased tissue will be controlled more by NO-based blood perfusion rather than by neuronal processes. That is, NO controlled temperature oscillations 158 will dominate over the attenuated neuronal temperature oscillations 160.

A second side effect of NO controlled blood perfusion is an increase in spatial homogeneity of skin temperature 162. That is, there will be less temperature variation in the skin surface temperature due to the NO-induced vasodilation of the capillary bed. NO controlled blood perfusion will occur at non-neuronal TRFs 164, as will be discussed in detail below. As with healthy tissue, the temperature of the skin overlying diseased tissue will create an IR flux 166 that can then be imaged by the dual-band IR imager 112.

The first embodiment of the present invention is based upon the average temperature of the imaged tissue. The first embodiment converts the first and second series of IR images into thermal images, i.e., converts each pixel from the IR image to a corresponding temperature. Each individual thermal image therefore is a two-dimensional array of temperatures and each of the first and second series of thermal images is a series of two-dimensional arrays of temperatures. At the preferred imaging rate of 30 to 60 images per second and a 10 to 60 second series of images, the first and second thermal images can readily include over 1000 individual thermal images. The first embodiment next subdivides the tissue area imaged into a number of subareas. These subareas correspond to two pixel by two pixel portions of the thermal images or larger. A preferred upper limit on the subarea size is an eight pixel by eight pixel subarea as larger areas will tend to average out any local variations that might indicate the presence of diseased tissue.

Figure 2:
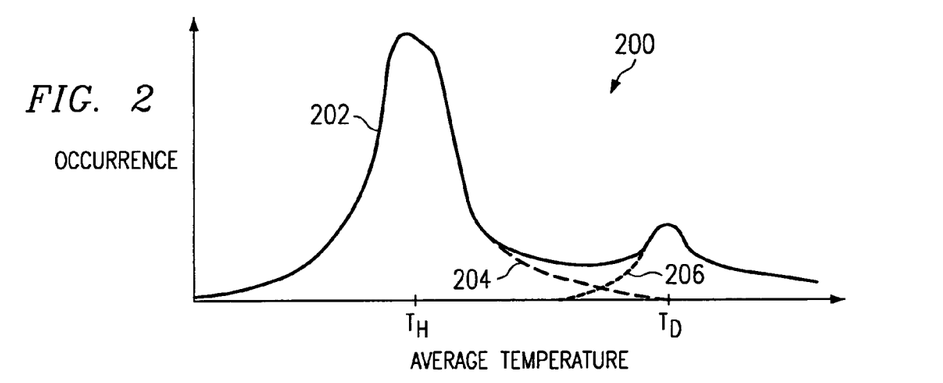
FIG. 2 is an average temperature histogram generated by a first embodiment of the present invention.

The first embodiment then finds the average temperature value for each of these subareas. This is done for each individual thermal image in both the first and the second series of thermal images resulting in first and second pluralities of average temperature values. These first and second pluralities of average temperature values are then analyzed in view of FIG. 2. FIG. 2 illustrates a histogram showing all of the average temperature values for the first plurality of average temperature values 200. Curve 202 is the composite curve showing the average temperature values for skin overlying both healthy and diseased tissue. Curve 204 corresponds to the average temperature values for the skin overlying a healthy region of tissue. Curve 204 therefore corresponds to skin whose underlying tissue is thermally regulated by neuronal control of blood perfusion. The peak temperature value for this healthy tissue is denoted $T_H$. In regions of skin overlying diseased or cancerous tissue, the average temperature value curve 206 is formed. Due to the generally vasodilated state of the capillary bed in diseased tissue, the average temperature value for these regions is greater. The higher peak average temperature value for these diseased regions is denoted by $T_D$.

A preliminary determination that a cancerous lesion may be present requires that a cluster of six adjacent subareas each have abnormal average temperature values. A first average temperature value for the first series of thermal images is calculated. This first average temperature value is preferably found by proportionately weighting each of the subareas based upon their size. In particular, when a spatial distribution of the first average temperature values within the cluster of six adjacent subareas is less than about 20% or more than about 100% of the first average temperature value, tissue corresponding to the cluster of six adjacent subareas is preliminarily determined to be diseased. This preliminary determination is confirmed if the same series of calculations and comparisons on the second series of thermal images yields the same cluster of six adjacent subareas.

Figure 3:
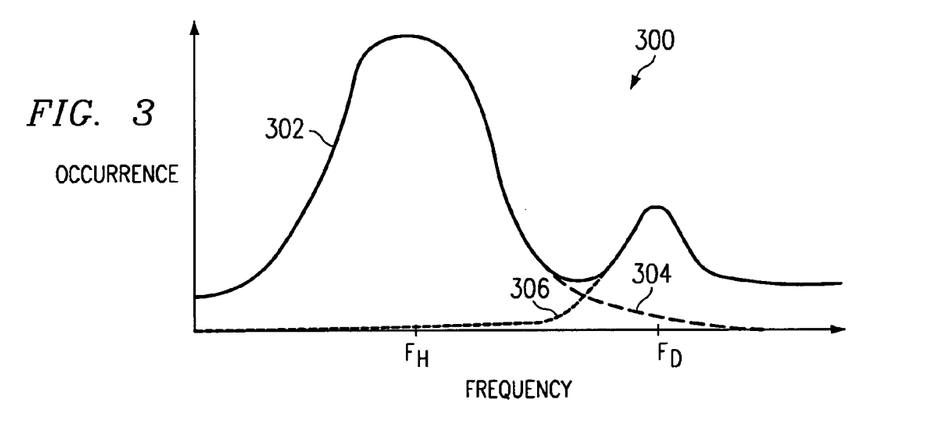
FIG. 3 is a contributing frequency histogram generated by second and third embodiments of the present invention.

As each of the first and second series of IR images is preferably taken periodically, TRFs can be determined. The second embodiment of the present invention makes use of these TRFs. FIG. 3 illustrates a TRF histogram for both healthy and diseased tissue 300. Curve 302 is a composite for both the healthy and diseased tissue while curve 304 corresponds to healthy tissue and curve 306 corresponds to diseased tissue. Curve 304 for healthy tissue reflects neuronal control blood perfusion and generally has a frequency of between 10 and 700 milliHertz. In contrast, curve 306 for diseased tissue reflects NO-based control of blood perfusion and has a higher frequency, generally in the range of 0.8 to 2.0 Hz.

The second embodiment makes use of the differences in TRFs by finding the contributing frequency for each subarea in the first series of thermal images. This contributing frequency may be determined by analyzing the average temperature value for a subarea based on the known periodic nature of the first series of thermal images. The preferred method to determine the contributing frequency is to subject the average temperature values to a fast Fourier transform that rapidly finds the frequency components or ranges of frequencies for a time varying signal. As shown in FIG. 3, while more healthy tissue subareas had a TRF of $F_H$, there is some variation about this frequency. However, very few healthy tissue subareas had a TRF as high as $F_D$, the strongest of the diseased tissue TRFs. Once the contributing frequency for each subarea using the first series of thermal images is determined, first lower and upper threshold frequencies are found, preferably by weighting each subarea based upon their size. As before, a cluster of six adjacent abnormal subareas leads to a preliminary diseased tissue diagnosis. In particular, when a spatial distribution of the contributing frequency of the cluster is less than the first lower threshold frequency or more than the first upper threshold frequency, tissue corresponding to the cluster is preliminarily diagnosed as being diseased. This preliminary diagnosis is confirmed if the same series of determinations and comparisons on the second series of thermal images yields the same cluster of six adjacent subareas.

The third embodiment is similar to the second embodiment in that it uses the contributing frequency of each subarea. In particular, the third embodiment uses the amplitude of the contributing frequencies. As shown in FIG. 3, the diseased tissue curve 306 has only a small frequency amplitude at $F_H$, thus providing another means for cancer discrimination. The third embodiment therefore searches for a cluster in which a spatial distribution of the amplitude of the contributing frequency is less than a first lower threshold amplitude or more than a first upper threshold amplitude. The first lower and upper threshold amplitudes are determined using the first series of thermal images and is preferably weighted by subarea size. As with the previous embodiments, the use of the second series of thermal images is used to confirm a preliminary diseased diagnosis from the first series of thermal images.

Figure 4:
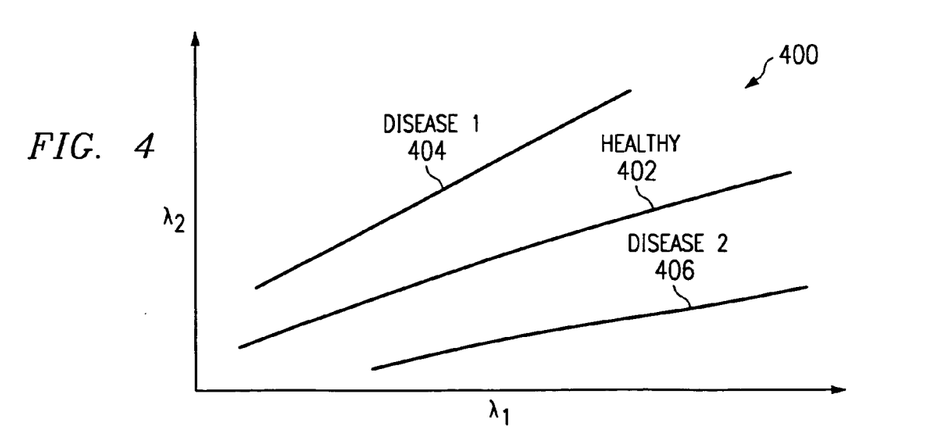
FIG. 4 is a correlation plot generated by fourth and fifth embodiments of the present invention.

In contrast to the first three embodiments that use the two series of thermal images sequentially, the fourth embodiment uses the two series of thermal images in parallel. FIG. 4 illustrates a series of correlation curves 400 for two different bands of IR wavelengths, the two bands centered around $\lambda_1$ and $\lambda_2$. The fourth embodiment includes taking a baseline radiance measurement of known healthy skin and tissue in the two different bands of IR wavelengths, thereby generating a healthy skin and tissue correlation curve 402. This healthy correlation curve 402 can be mathematically defined most simply in terms of a slope and an intercept, that is $\lambda_2=m_H\lambda_1+b_H$. It should be noted that depending upon the wavelengths within the two bands of IR wavelengths, the properties of the skin and underlying tissue, etc., additional terms might be required to more accurately describe the correlation. In the simple slope and intercept form, the precise values for $m_H$ and $b_H$ will likely be a function of the skin and the underlying tissue. For example, the $m_H$ and $b_H$ values for a breast cancer screening will likely be different from the $m_H$ and $b_H$ values for a bony structure such as the wrist or ankle. Once the appropriate healthy correlation curve 402 is determined, the subareas within the first and second series of thermal images will also be correlated. This correlation may produce subareas having diseased correlation curve 404 or 406. Diseased correlation curve 404 may be described as $\lambda_2=m_{D1}\lambda_1+b_{D1}$, while diseased correlation curve 406 may be described as $\lambda_2=m_{D2}\lambda_1+b_{D2}$. The fourth embodiment then compares the slope $m_{D1}$ or $m_{D2}$ with $m_H$. If a spatial distribution of the $m_{D1}$ or $m_{D2}$ values for a cluster are different than $m_H$, then the tissue corresponding to the cluster is determined to be diseased. How different the slope values will be will depend upon the types of underlying tissue as noted above, as well as the specific wavelengths $\lambda_1$ and $\lambda_2$ chosen.

The radiance measurements of healthy skin taken for the fourth embodiment may be made as a function of integration time for the dual-band IR imager 112, the temperature of the skin and tissue being imaged, or a combination thereof. The temperature of the skin and tissue can be varied by directing either a warming or a cooling stream of air on the skin and tissue resulting in thermal stress to the skin and tissue. Alternatively, this thermal stress may be induced by directing a flow of water vapor to the skin and tissue. While this thermal stress finds particular application with the fourth (and fifth) embodiments, it can readily be used in conjunction with the other embodiments as well.

Due to the oscillatory nature of thermal regulation, the sensitivity of the fourth (and fifth) embodiments can be increased. By finding the contributing frequency for each of the subareas, the correlation between the two series of thermal images can be made at neuronal frequencies or at NO modulation frequencies. It is anticipated that correlations made at NO modulation frequencies will be especially sensitive for discriminating healthy versus diseased skin and tissue regions.

While the fourth embodiment uses the slope of the correlation between the two series of thermal images, the fifth embodiment uses the intercept of the correlation between the two series of thermal images. To this end, the fifth embodiment compares $b_{D1}$ or $b_{D2}$ with $b_H$. When the spatial distribution of $b_{D1}$ or $b_{D2}$ for a cluster are different from $b_H$, tissue corresponding to the cluster is diagnosed as being diseased. As before, this difference is a function of the underlying tissue and the specific wavelengths chosen.

Figure 5:
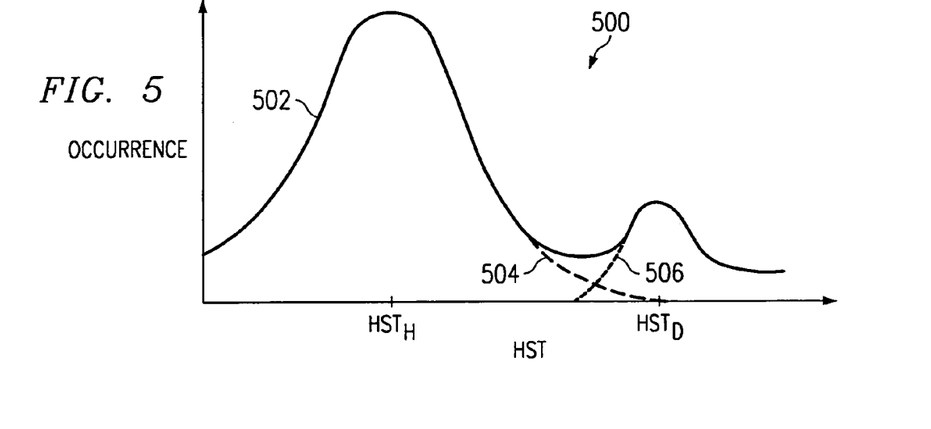
FIG. 5 is an HST value histogram generated by sixth and seventh embodiments of the present invention.

The sixth embodiment of the present invention is based upon detectable differences in the HST between healthy and diseased skin and tissue. The HST for a subarea is found by determining both the average temperature value and the temperature standard deviation and then dividing the average temperature value by the temperature standard deviation. The HST is found for each subarea for each of the first series of thermal images. FIG. 5 shows the resultant histogram 500 of HST values from the first series of thermal images for the skin overlying both healthy and diseased tissue. Curve 502 is the overall HST curve while curve 504 corresponds to healthy skin and tissue while curve 506 corresponds to diseased skin and tissue. The temperature standard deviation found in diseased tissue is lower than that of healthy tissue due to the overall vasodilated state of the capillary bed. This lower standard deviation results in higher HST values for diseased skin and tissue regions, centered about $HST_D$ as shown in FIG. 5. In contrast, healthy skin and tissue temperature is controlled by neuronal processes that include both vasodilation and vasoconstriction. This results in wider variations in skin temperature, larger temperature standard deviations and therefore smaller HST values. FIG. 5 shows the healthy skin and tissue regions to have HST values centered about $HST_H$. An overall first average HST for the first series of thermal images is also computed. A preliminary diseased tissue diagnosis is made when spatial distribution of a cluster of six adjacent subareas have HST values of less than about 20% or more than about 100% of the first average HST. This preliminary diagnosis is confirmed if the same series of calculations and comparisons on the second series of thermal images yields the same cluster of six adjacent subareas.

The seventh embodiment makes use of the differences in TRFs of the HST values by finding the contributing frequency for each subarea in the first plurality of HST values. The seventh embodiment will generate a frequency histogram similar to that of FIG. 3 in that healthy tissue subareas will have a TRF of HST values with some variation about a healthy tissue center frequency. Likewise, diseased tissue subareas will have TRF of HST values with some variation about a higher diseased tissue center frequency. Once the contributing TRF of HST values for each subarea using the first series of thermal images is determined, a first average contributing frequency is found. A cluster of six adjacent abnormal subareas leads to a preliminary diseased tissue diagnosis. In particular, when a spatial distribution of the magnitude of the contributing TRF of HST values of the cluster is less than about 20% or more than about 100% of the first average contributing frequency, tissue corresponding to the cluster is preliminarily diagnosed as being diseased. This preliminary diagnosis is confirmed if the same series of determinations and comparisons on the second series of thermal images yields the same cluster of six adjacent subareas.

Figure 6:
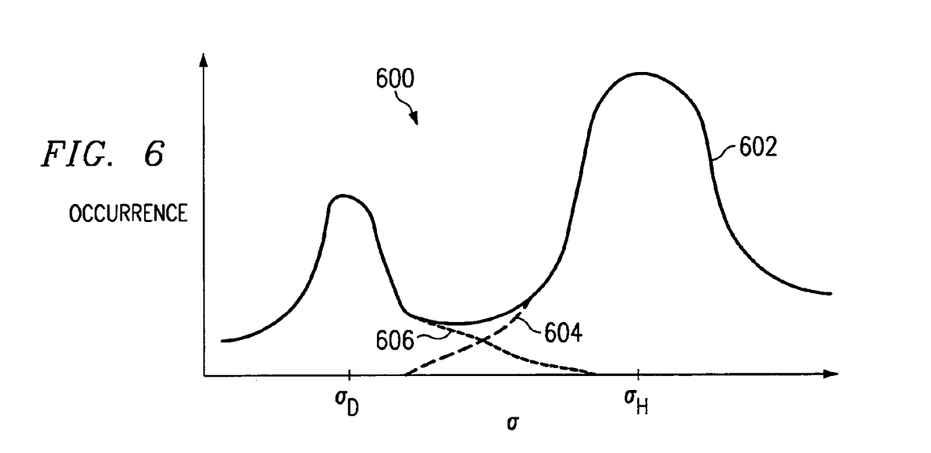
FIG. 6 is a temperature standard deviation histogram generated by an eighth embodiment of the present invention
Figure 7:
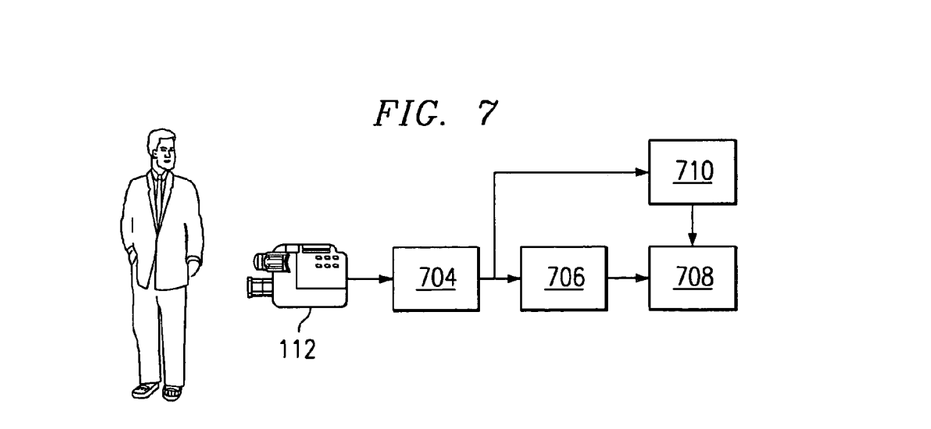
FIG. 7 is a block diagram of an apparatus for implementing the first through third embodiments of the present invention.

FIG. 6 illustrates a temperature standard deviation histogram 600 employed by the eighth embodiment of the present invention. The eighth embodiment requires determining the temperature standard deviation for each of the subareas for each one of the first series of thermal images. Curve 602 corresponds to the resultant overall histogram for the temperature standard deviations and is a combination of a curve 604 representing the temperature standard deviations for healthy skin and tissue and curve 606 representing the temperature standard deviations for diseased skin and tissue. The standard deviation for diseased skin and tissue will be lower as noted above due to the generally vasodilated state of the capillary bed leading to more constant temperatures relative to skin and tissue under neuronal controlled blood perfusion. A preliminary diagnosis of diseased skin and tissue corresponding to a cluster of six adjacent subareas requires the cluster to have a spatial distribution of temperature standard deviation of less than about 20% or more than about 100% of a first average temperature standard deviation based upon the first series of thermal images. The preliminary diagnosis based upon temperature standard deviation is confirmed if the same series of determinations and comparisons on the second series of thermal images yields the same cluster of six adjacent subareas.

Each of the embodiments will now be described in reference to FIGS. 7 through 10. The first through third embodiments are illustrated by the block diagram shown in FIG. 7. In each of the first through third embodiments, two series of IR images of the tissue are recorded in two corresponding different bands of IR wavelengths by the dual-band IR imager 112. The two series of IR images are then converted by a converter 704 into two series of thermal images. An averager 706 then determines a series of average temperatures for each of the subareas using both series of thermal images. The averager 706 also determines an overall average temperature using both series of thermal images. All of this average temperature information is then analyzed by an analyzer 708 in the first embodiment. In the second embodiment, the two series of thermal images undergo frequency analysis, i.e., the contributing frequencies for the subareas are determined, by a frequency analyzer 710. The contributing frequencies are then analyzed by the analyzer 708 to determine if any clusters indicate the presence of diseased tissue based upon contributing frequencies. Like the second embodiment, the third embodiment uses the frequency analyzer 710. The third embodiment requires the analyzer to analyze the amplitude of the contributing frequencies and any clusters having unusual frequency amplitudes may be diagnosed as corresponding to diseased tissue.

Figure 8:
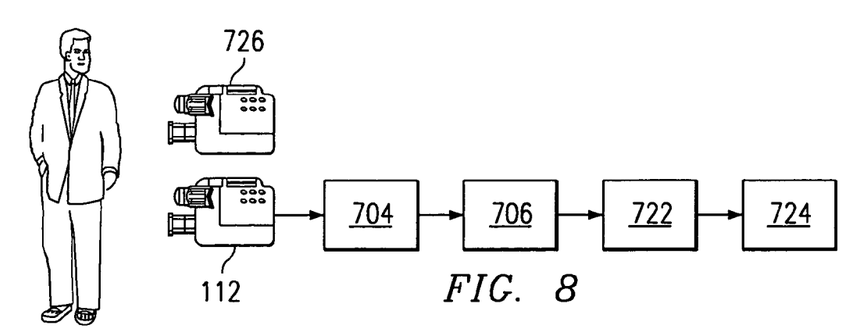
FIG. 8 is a block diagram of an apparatus for implementing the fourth and fifth embodiments of the present invention.

The fourth and fifth embodiments are illustrated in the block diagram of FIG. 8. As with the first three embodiments, two series of IR images of the tissue are recorded in two corresponding different bands of IR wavelengths by the dual-band IR imager 112. The two series of IR images are then converted by the converter 704 into two series of thermal images. The averager 706 then determines a series of average temperatures for each of the subareas using both series of thermal images. The dual-band IR imager 112 also records radiance images in both bands of IR wavelengths, which are subsequently converted into thermal images. Both sets of average temperature data and the radiance image data are correlated by a correlator 722. An analyzer 724 then analyzes the correlation data produced by the correlator 722. In the fourth embodiment, the analyzer 724 analyzes the slope of the correlation data while in the fifth embodiment the analyzer 724 analyzes the intercept of the correlation data. FIG. 8 also illustrates an element 726 for subjecting tissue to a thermal stress. As noted above, the element 726 can create this thermal stress by directing a stream of warm or cool air over the tissue or by directing a mist at the tissue. While the element 726 is illustrated only in FIG. 8 corresponding to the apparatus for implementing the fourth and fifth embodiments, it can readily be included apparatuses for implementing the first through third and sixth through eighth embodiments.

Figure 9:
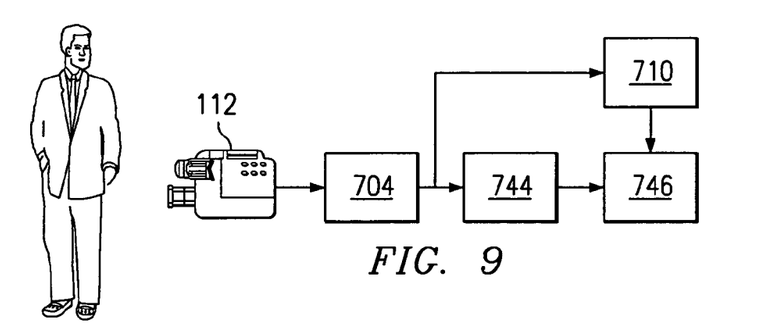
FIG. 9 is a block diagram of an apparatus for implementing the sixth and seventh embodiments of the present invention.

An apparatus for implementing the sixth and seventh embodiments is illustrated in block fashion in FIG. 9. As with the first five embodiments, two series of IR images of the tissue are recorded in two corresponding different bands of IR wavelengths by the dual-band IR imager 112. The two series of IR images are then converted by the converter 704 into two series of thermal images. In the sixth embodiment, the two series of thermal images are then processed by the processor 744. The processor 744 determines average temperatures and standard deviations for each of the subareas using both series of thermal images. The processor 744 then determines HST values for each of the subareas for both series of thermal images. Lastly, the processor 744 determines the average HST value for both series of thermal images. An analyzer 746 then analyzes this HST data to determine if any clusters correspond to diseased tissue. In the seventh embodiment, the two series of thermal images undergo frequency analysis by the frequency analyzer 710. The resultant frequency analyzed data is then analyzed by the analyzer 746 to determine of diseased tissue is present.

Figure 10:
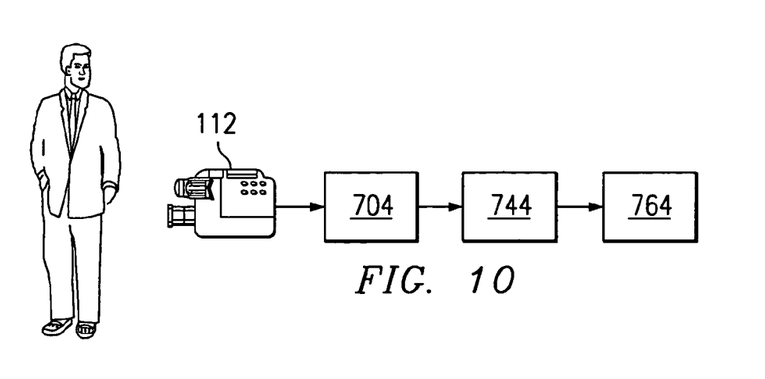
FIG. 10 is a block diagram of an apparatus for implementing the eighth embodiment of the present invention.

FIG. 10 illustrates the various blocks required for implementing the eighth embodiment of the present invention. Two series of IR images of the tissue are recorded in two corresponding different bands of IR wavelengths by the dual-band IR imager 112. The two series of IR images are then converted by a converter 704 into two series of thermal images. These two series of thermal images then undergo a series of processes by the processor 744 described above. The various averaged data is then analyzed by an analyzer 764. In the eighth embodiment, the analyzer 764 determines if any clusters have abnormal standard deviations that would indicate the presence of diseased tissue.

The diagnostic system 110, and in particular, the dual-band IR imager 112 will now be described in greater detail. The first and second bands of IR wavelengths detected by the dual-band IR imager 112 are preferably within the long wavelength IR (LWIR), which corresponds to radiation having a wavelength of eight to twelve microns. For example, the first band of IR wavelengths might cover the wavelength range of eight to nine microns while the second band of IR wavelengths might cover from ten to eleven microns. The LWIR is preferred as the human body IR emissions peak within this range of wavelengths. The first and second bands of IR wavelengths could alternatively be in the middle wavelength IR (MWIR) corresponding to radiation having a wavelength of three to five microns. As a further alternative, the two bands of IR wavelengths could include one in the LWIR and one in the MWIR.

The dual-band IR imager 112 may be formed in one of several ways. The dual-band IR imager 112 could include two single-band IR photodetector arrays, each sensitive to different bands of IR wavelengths. Alternatively, the two single-band IR photodetector arrays could be identical with the different bands of IR wavelength response due to filters. Using two single band IR photodetectors will require the use of a beam splitter to cause spatially registered images to be focused on each of the single-band IR photodetector arrays. While the use of two single-band IR photodetector arrays will probably decrease the cost of each single-band IR photodetector array, the overall system cost will likely increase. Such a two photodetector array-based dual-band IR imager 112 will require the aforementioned beamsplitter, and probably two separate coolers as each single-band IR photodetector array will require cooling. Such a two photodetector array-based dual-band IR imager will also require very tight tolerances to ensure that the image is truly spatially registered on both photodetector arrays, thereby reducing manufacturability.

A single dual-band IR photodetector array appears more feasible and manufacturable. Several dual-band photodetector technologies have been demonstrated including those using HgCdTe and GaAs-based multiple quantum well (MQW) semiconductor materials. Dual-band photodetectors using HgCdTe semiconductor materials have high quantum efficiencies, but place strict requirements on the HgCdTe manufacturing process. While dual-band HgCdTe photodetectors operating in the MWIR and LWIR have shown excellent performance, the use of HgCdTe semiconductor material for the preferred LWIR-LWIR configuration places extremely strict requirements on the starting HgCdTe semiconductor material. For these reasons, it appears unlikely that a commercial HgCdTe dual-band IR camera is feasible using current manufacturing technology.

GaAs-based MQW semiconductor material appears to be a more manufacturable technology and is thus preferable for the present invention. The GaAs-based starting material is commercially available from several sources and the fabrication processes are in use in a number of facilities. GaAs-based MQW semiconductor material may be fabricated into quantum well IR photodetectors (QWIPs) and enhanced QWIPs (EQWIPs). Dual-band QWIPs and EQWIPs have been demonstrated to date with the EQWIP offering better sensitivity due to its resonant optical cavity and reduced noise. Various embodiments of the EQWIP are described and claimed in U.S. Pat. Nos. 5,539,206, 6,133,571, 6,157,042, and 6,355,939 and are hereby incorporated by reference. Additional preferred embodiments of the EQWIP are described in copending application numbers 21201 and 21301.

The present invention, by imaging a human being, encounters problems should the patient move during the image taking portion of the process. To minimize this effect, the images for the two different series of IR images are preferably taken in an alternating fashion. That is, first an IR image is taken from the first band of IR wavelengths and then an IR image is taken from the second band of IR wavelengths. By alternating the IR wavelength bands, the correlation between the first image in both series of IR images increases when compared to taking all of the first series of IR images over the course of 10 to 60 seconds and then taking all of the second series of IR images. To further minimize problems due to patient motion, the imaging rate should be relatively high, preferably in the range of 30 to 60 Hz or greater. An added benefit of the increased imaging rate is that any of the embodiments using frequency-based analysis will have increased frequency resolution.

The computer 114 within the diagnostic system 110 will be required to store significant quantities of data and undertake substantial numerical processing. The computer 114 will need to store several thousands of individual IR images and thermal images for each patient. As each of these could include 640 pixels by 480 pixels-worth of data, a rather sizeable hard disk drive and large amount of RAM will be beneficial. Due to the substantial amount of numerical processing that will be undertaken, a separate numerical processing board may be advantageous.

Although the present invention has been fully described by way of examples with reference to the accompanying drawings, it is to be noted that various changes and modifications will be apparent to those skilled in the art. Therefore, such changes and modifications should be construed as being within the scope of the invention.

What is claimed is:

1. A method of detecting diseased tissue comprising:
    recording first and second series of infrared images of a predetermined area of tissue, the first and second series of infrared images recorded in respective first and second bands of infrared wavelengths, the second band of infrared wavelengths different from the first band of infrared wavelengths;
    converting the first and second series of infrared images into corresponding first and second series of thermal images having a plurality of subareas;
    determining a first plurality of average temperature values for each of the plurality of subareas, each of the first plurality of average temperature values for each of the plurality of subareas determined from a corresponding one of the first series of thermal images;
    determining a first average temperature using the first plurality of average temperature values;
    determining a second plurality of average temperature values for each of the plurality of subareas, each of the second plurality of average temperature values for each of the plurality of subareas determined from a corresponding one of the second series of thermal images;
    determining a second average temperature using the second plurality of average temperature values; and
    analyzing the first and second pluralities of average temperature values for each of the plurality of subareas,
    wherein when a spatial distribution of the first plurality of average temperature values corresponding to a cluster comprising at least six adjacent subareas is less than about 20% or more than about 100% of the first average temperature, tissue corresponding to the cluster is preliminarily determined to be diseased, and
    wherein when the tissue corresponding to the cluster is preliminarily determined to be diseased and when a spatial distribution of the second plurality of average temperature values corresponding to the cluster is less than about 20% or more than about 100% of the second average temperature, tissue corresponding to the cluster is confirmed to be diseased.

2. A method of detecting diseased tissue in accordance with claim 1, wherein analyzing the first and second pluralities of average temperature values for each of the plurality of subareas further includes:
    determining a first contributing frequency of the first plurality of average temperature values for each of the plurality of subareas using the first series of thermal images;
    determining first lower and upper threshold frequencies using the first contributing frequency of each of the subareas;
    determining a second contributing frequency of the second plurality of average temperature values for each of the plurality of subareas using the second series of thermal images; and
    determining second lower and upper threshold frequencies using the second contributing frequency of each of the subareas,
    wherein when a spatial distribution of first contributing frequencies of the cluster is less than the first lower threshold frequency or more than the first upper threshold frequency, tissue corresponding to the cluster is preliminarily determined to be diseased, and
    wherein when tissue corresponding to the cluster is preliminarily determined to be diseased and when a spatial distribution of second contributing frequencies of the cluster is less than the second lower threshold frequency or more than the second upper threshold frequency, tissue corresponding to the cluster is confirmed to be diseased.

3. A method of detecting diseased tissue in accordance with claim 1, wherein analyzing the first and second pluralities of average temperature values for each of the plurality of subareas further includes:
    determining a first contributing frequency of the first plurality of average temperature values for each of the plurality of subareas using the first series of thermal images;
    determining a first average amplitude using the first contributing frequency for the plurality of subareas;
    determining a second contributing frequency of the second plurality of average temperature values for each of the plurality of subareas using the second series of thermal images; and
    determining a second average amplitude using the second contributing frequency for the plurality of subareas,
    wherein when a spatial distribution of first amplitudes of first contributing frequencies of the cluster is less than about 20% or more than about 100% of the first average amplitude, tissue corresponding to the cluster is preliminarily determined to be diseased, and
    wherein when tissue corresponding to the cluster is preliminarily determined to be diseased and when a spatial distribution of second amplitudes of second contributing frequencies of the cluster is less than about 20% or more than about 100% of the second average amplitude, tissue corresponding to the cluster is confirmed to be diseased.

4. A method of detecting diseased tissue in accordance with claim 1, wherein analyzing the first and second pluralities of average temperature values for each of the plurality of subareas further includes analyzing the first and second pluralities of average temperature values for each of the plurality of subareas using a fast Fourier transform analysis.

5. An apparatus for detecting diseased tissue comprising:
    an imager for recording first and second series of infrared images of a predetermined area of tissue, the first and second series of infrared images recorded in respective first and second bands of infrared wavelengths, the second band of infrared wavelengths different from the first band of infrared wavelengths;
    a converter for converting the first and second series of infrared images into corresponding first and second series of thermal images having a plurality of subareas;
    an averager for determining a first plurality of average temperature values for each of the plurality of subareas, each of the first plurality of average temperature values for each of the plurality of subareas determined from a corresponding one of the first series of thermal images, the averager for determining a first average temperature using the first plurality of average temperature values, the averager for determining a second plurality of average temperature values for each of the plurality of subareas, each of the second plurality of average temperature values for each of the plurality of subareas determined from a corresponding one of the second series of thermal images, and the averager for determining a second average temperature using the second plurality of average temperature values; and an analyzer for analyzing the first and second pluralities of average temperature values for each of the plurality of subareas, wherein when a spatial distribution of the first plurality of average temperature values corresponding to a cluster comprising at least six adjacent subareas is less than about 20% or more than about 100% of the first average temperature, tissue corresponding to the cluster is preliminarily determined to be diseased, and wherein when the tissue corresponding to the cluster is preliminarily determined to be diseased and when a spatial distribution of the second plurality of average temperature values corresponding to the cluster is less than about 20% or more than about 100% of the second average temperature, tissue corresponding to the cluster is confirmed to be diseased.

6. An apparatus for detecting diseased tissue in accordance with claim 5, further comprising a frequency analyzer for determining a first contributing frequency of the first plurality of average temperature values for each of the plurality of subareas using the first series of thermal images, the frequency analyzer for determining first lower and upper threshold frequencies using the first contributing frequency of each of the subareas, the frequency analyzer for determining a second contributing frequency of the second plurality of average temperature values for each of the plurality of subareas using the second series of thermal images, and the frequency analyzer for determining second lower and upper threshold frequencies using the second contributing frequency of each of the subareas, wherein the analyzer is further adapted for analyzing the first and second contributing frequencies for each of the plurality of subareas, wherein when a spatial distribution of first contributing frequencies of the cluster is less than the first lower threshold frequency or more than the first upper threshold frequency, tissue corresponding to the cluster is preliminarily determined to be diseased, and wherein when tissue corresponding to the cluster is preliminarily determined to be diseased and when a spatial distribution of second contributing frequencies of the cluster is less than the second lower threshold frequency or more than the second upper threshold frequency, tissue corresponding to the cluster is confirmed to be diseased.

7. An apparatus for detecting diseased tissue in accordance with claim 5, further comprising a frequency analyzer for determining a first contributing frequency of the first plurality of average temperature values for each of the plurality of subareas using the first series of thermal images, the frequency analyzer for determining a first average amplitude using the first contributing frequency for the plurality of subareas, the frequency analyzer for determining a second contributing frequency of the second plurality of average temperature values for each of the plurality of subareas using the second series of thermal images, and the frequency analyzer for determining a second average amplitude using the second contributing frequency for the plurality of subareas, wherein the analyzer is further adapted for analyzing the first and second contributing frequencies for each of the plurality of subareas, wherein when a spatial distribution of first amplitudes of first contributing frequencies of the cluster is less than about 20% or more than about 100% of the first average amplitude, tissue corresponding to the cluster is preliminarily determined to be diseased, and wherein when tissue corresponding to the cluster is preliminarily determined to be diseased and when a spatial distribution of second amplitudes of second contributing frequencies of the cluster is less than about 20% or more than about 100% of the second average amplitude, tissue corresponding to the cluster is confirmed to be diseased.

8. An apparatus for detecting diseased tissue in accordance with claim 5, wherein the analyzer further uses a fast Fourier transform analysis.

* * * * *